April 19, 1955 E. S. BOERNER Plant Pat. 1,379
ROSE PLANT
Filed May 3, 1954
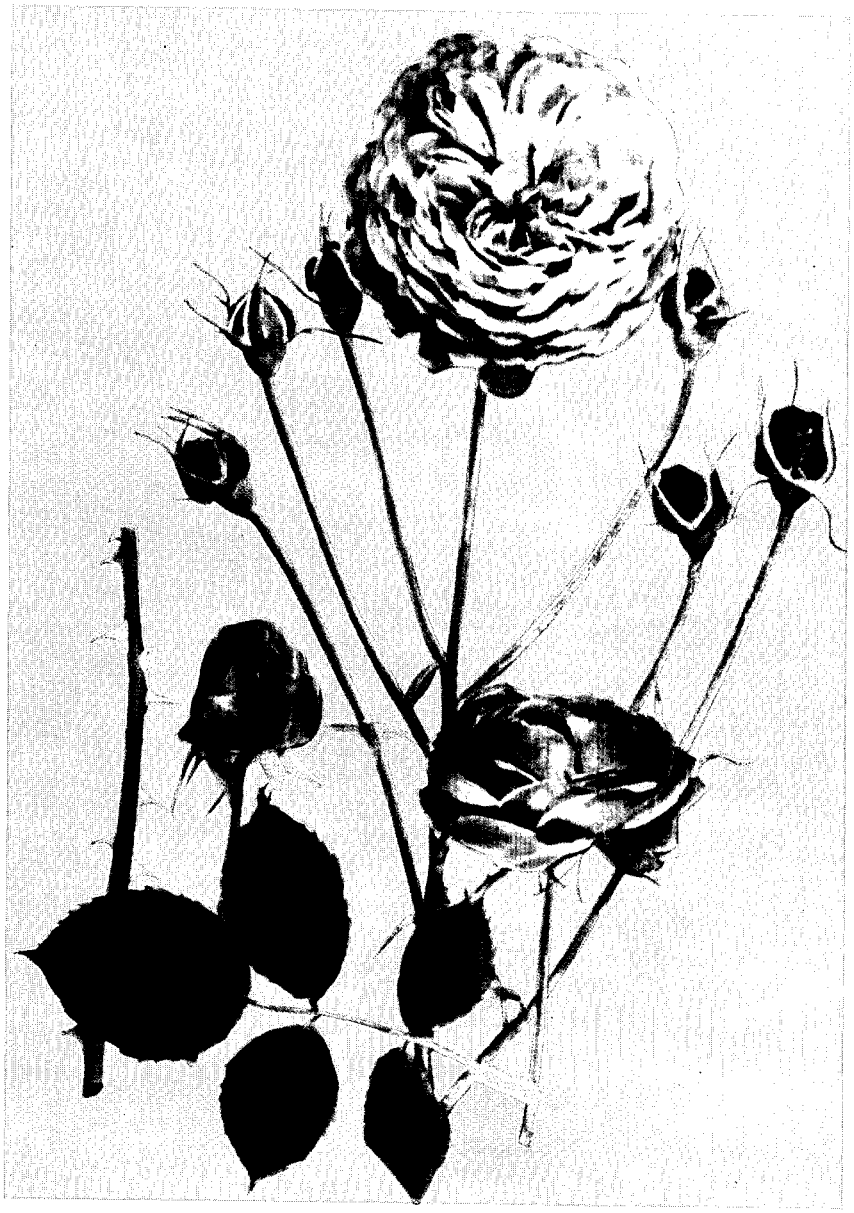
Inventor
E S Boerner
By: Robb & Robb
Attorneys United States Patent Office Plant Pat. 1,379

Patented Apr. 19, 1955

1,379

ROSE PLANT

Eugene S. Boerner, Newark, N. Y., assignor to Jackson & Perkins Company, Newark, N. Y., a corporation of New York Application May 3, 1954, Serial No. 427,401

1 Claim. (Cl. 47—61)

The present invention relates to a new and distinct variety of rose plant of the large-flowered polyantha class, which was originated by me by crossing the variety "Chatter" (Plant Patent No. 739) with the variety "Red Pinocchio" (Plant Patent No. 812).

The primary objective in making this cross was to try to get some of the flowering characteristics and the lasting qualities of the blooms of "Chatter" into the stronger and more vigorous plants of the variety "Red Pinocchio," as by combining the best qualities of the two parent varities. This objective was fully achieved, as evidenced by the fact that the flowers of my new variety are larger and more double than those of "Red Pinocchio," and the flowers of my new variety have a greater lasting quality, while at the same time, the plants of my new variety grow taller than either parent variety.

More particularly speaking, my new variety is primarily characterized as to novelty by the distinctive carmine general color tonality of its flowers, the relatively large size of its flowers, and their habit of being borne in pyramidal heads of very long lasting quality; the flower buds are double and rounded, and are overlapped with sepals; and the flowers have a distinctive fully open form. These features, taken together, represent a unique and desirable combination which definitely distinguishes my new variety from its parents, as well as from all other varieties of which I am aware.

Asexual reproduction of my new variety by budding at Newark, New York, and also at Pleasanton, California, shows that the foregoing characteristics and distinctions come true to form and are established and transmitted through succeeding propagations.

The accompanying drawing shows a typical pyramidal cluster of flowers of my new variety in different stages of development, as well as other typical specimens of the flowers, foliage and stems of my new variety, with the specimens depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Chatter."
- *Pollen parent.*—"Red Pinocchio."

Classification:
- *Botanic.*—Large-flowered polyantha.
- *Commercial.*—Floribunda.

FLOWER (Observations made from specimens grown outdoors at Newark, New York in the early part of the month of July, and in the early afternoon.)

Blooming habit: Recurrent—continuous.

Bud:
- *Size.*—Large.
- *Form.*—Ovoid; is not affected by wet or hot weather.
- *Color.*—When sepals first divide—Oxblood Red, Plate 1. When petals begin to unfurl—Oxblood Red, Plate 1, overcast with Carmine, Plate 1. When half brown: Inside of petals—Carmine, Plate 1, lightly overcast with Spectrum Red, Plate 1; reverse of petals—Carmine, Plate 1, lightly overcast with Pomegranate Purple, Plate 12.

- *Sepals.*—Slight branched; curl back when petals begin to unfurl. Color: Inside—Kildare Green, Plate 31; outside—Parrot Green, Plate 6.
- *Calyx.*—Color—Lettuce Green, Plate 5. Shape—apple. Size small. Aspect — smooth. Odor when rubbed—none.
- *Peduncle.*—Length — medium. Aspect — smooth. Strength—erect; slender. Color—Lettuce Green, Plate 5.
- *Opening.*—Opens up well; is not affected by adverse weather conditions.

Bloom:
- *Size.*—Medium; average size when fully expanded—from 2½ inches to 3 inches.
- *Borne.*—Several together and in pyramidal clusters.
- *Stems.*—Medium length; normal strength.
- *Form (when first open).* — Globular. Permanence—outer petals curl back when fully open.
- *Petalage.*—Very double; from 65 to 70 petals under normal conditions.
- *Color.*—Center of flower—Carmine, Plate 1. Outer petals—Carmine, Plate 1, lightly overcast with Pomegranate Purple, Plate 12. Base of petals (aiglet)—Citron Yellow, Plate 16. Inside of petals—Carmine, Plate 1, lightly overcast with Rose Red, Plate 12. Reverse of petals—Pomegranate Purple, Plate 12, lightly overcast with Tyrian Rose, Plate 12. General tonality from a distance—Carmine, Plate 1.
- *Discoloration.*—General tonality at end of first day—Carmine, Plate 1. Second day—Carmine, Plate 1, lightly overcast with Rose Red, Plate 12. Third day—Carmine, Plate 1, lightly overcast with Pomegranate Purple, Plate 12.

Petals:
- *Texture.*—Thick; is not affected by wet or hot weather.
- *Appearance.*—Inside—velvety; outside—shiny.
- *Form.*—Oval.
- *Arrangement.* — Imbricated (regularly arranged shingle-like).
- *Petaloids in center.*—Few; small.
- *Persistence.*—Drop off cleanly.
- *Fragrance.*—Moderate. Nature—tea rose.
- *Lasting quality.*—On the plant—long. As cut flowers—long.

GENITAL ORGANS

Stamens, anthers: Medium size; many; mixed with petaloids. Color—Amber Yellow, Plate 16.
Stamens, filaments (threads): Medium length. Color—Picric Yellow, Plate 4.
Pollen: Color—Straw Yellow, Plate 16.
Styles: Bunched; uneven length; medium length; thin.
Stigmas: Color—Barium Yellow, Plate 16.
Ovaries: All enclosed in calyx.
Hips: None.
Seeds: None.

PLANT

Form: Bush.
Growth: Vigorous; upright.
Foliage: 5 to 7 leaflets.
- *Size.*—Medium.
- *Quantity.*—Normal.
- *Color.*—New foliage: Upper side—Oil Green, Plate 5, with serrations of Oxblood Red, Plate 1; under side—light Cress Green, Plate 31. Old foliage: Upper side—Yew Green, Plate 31; under side—light Elm Green, Plate 17.
- *Shape.*—Oval pointed.
- *Texture.*—Upper side—smooth; under side—smooth.
- *Ribs and veins.*—Ordinary.
- *Edge.*—Serrated (saw-toothed).
- *Serration.*—Double and single; small.
- *Leaf stem.*—Color—light Hellebore Green, Plate 17. Under side—smooth.
- *Stipules.*—Medium length; smooth.

Wood:
- *New wood.*—Color—Absinthe Green, Plate 31. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form—flat base; medium length; some straight and some hooked downward. Color (when young)—Buff—Pink, Plate 28. Position—irregular.

*Prickles.*—Quantity: On main stalks—none; on laterals—none.

*Short needles.*—Quantity: On main stalks—none; on laterals—none.

I claim:

A new and distinct variety of rose plant of the large-flowered polyantha class, substantially as herein shown and described, characterized particularly as to novelty by the distinctive carmine general color tonality of its flowers, the relatively large size of its flowers and their habit of being borne in pyramidal heads of very long lasting quality, the rounded, double buds which are overlapped with sepals, and the distinctive fully open form of the flowers.

No references cited.